(12) United States Patent
Jung et al.

(10) Patent No.: US 8,314,259 B2
(45) Date of Patent: Nov. 20, 2012

(54) METHOD OF MANUFACTURING GLYCEROL CARBONATE

(75) Inventors: Kwang Seop Jung, Seoul (KR); Jae Hyun Kim, Seoul (KR); Jung Hee Cho, Seoul (KR); Duk Ki Kim, Seoul (KR)

(73) Assignee: GS Caltex Corporation, Seoul (KR)

( * ) Notice: Subject to any disclaimer, the term of this patent is extended or adjusted under 35 U.S.C. 154(b) by 165 days.

(21) Appl. No.: 12/677,685

(22) PCT Filed: Sep. 11, 2008

(86) PCT No.: PCT/KR2008/005361
§ 371 (c)(1),
(2), (4) Date: Mar. 11, 2010

(87) PCT Pub. No.: WO2009/035269
PCT Pub. Date: Mar. 19, 2009

(65) Prior Publication Data
US 2010/0209979 A1      Aug. 19, 2010

(30) Foreign Application Priority Data
Sep. 12, 2007   (KR) .................. 10-2007-0092407

(51) Int. Cl.
*C07D 317/08*         (2006.01)

(52) U.S. Cl. ......................................................... 549/229
(58) Field of Classification Search ................... 549/229
See application file for complete search history.

(56) References Cited

U.S. PATENT DOCUMENTS
6,025,504 A      2/2000   Claude et al.
7,045,579 B2 *   5/2006   Van Den Berg et al. ...... 525/350

FOREIGN PATENT DOCUMENTS
WO         WO 93/09111 A2     5/1993

OTHER PUBLICATIONS

Sang Cheol Kim et al., Lipase-catalyzed synthesis of glycerol carbonate from renewable . . . , Journal of Molecular Catalysis B: Enzymatic, vol. 49, pp. 75-78, Aug. 25, 2007.

* cited by examiner

*Primary Examiner* — Maryam Monshipouri
(74) *Attorney, Agent, or Firm* — Reinhart Boerner Van Deuren P.C.

(57) ABSTRACT

Disclosed is a method of manufacturing a glycerol carbonate (GC). The method includes a bio-catalyst reaction for generating the GC and byproducts generated by reacting a reactant solution using a lipase of a bio-catalyst. In this instance, the reactant solution is prepared by adding glycerol, a glycerol-containing composition, or a dimethyl carbonate (DMC) in a reaction solvent.

8 Claims, 7 Drawing Sheets

GLYCEROL    DMC(Dimethyl Carbonate)    Glycerol Carbonate(GC)

METHOD OF MANUFACTURING GLYCEROL CARBONATE

Cross-reference to related patent applications

This patent application is the National Stage of International Application No. PCT/KR2008/005361, filed Sep. 11, 2008, that claims the benefit of Korean Application No. 10-2007-0092407, filed Sep. 12, 2007, the entire teachings and disclosure of which are incorporated herein by reference thereto.

TECHNICAL FIELD

The present invention relates to a method of manufacturing glycerol carbonate (GC), and more particularly, to a method of manufacturing GC which may provide excellent reaction stability and high efficiency upon synthesis of GC from glycerol.

BACKGROUND ART

Currently, studies for bio-diesel are actively made owing to an increase in interests for environmental-friendly energy businesses. Thereby, productivity of the bio-diesel may increase every year.

Along with an increase in the yield of the bio-diesel, supply quantities of byproducts generated due to production of the bio-diesel may be overly increased. As a representative example of the by-products of the bio-diesel, glycerol may be given.

The glycerol is possible to be transformed into various glycerol derivatives, for example, glycerol carbonate, epichlorohydrin, glycerol ether, 1,3-propane, and the like.

In particular, the glycerol carbonate is limpid and harmless at room temperature, and may be utilized as various applications. For example, the glycerol carbonate may be used as a main ingredient of an electrolyte of a secondary battery, a surfactant, various coating agents, medical goods, cosmetics, a composition for removing paint, and the like.

As a method for synthesizing the glycerol carbonate from glycerol, Equations 1 to 3 as below are provided, which are represented as

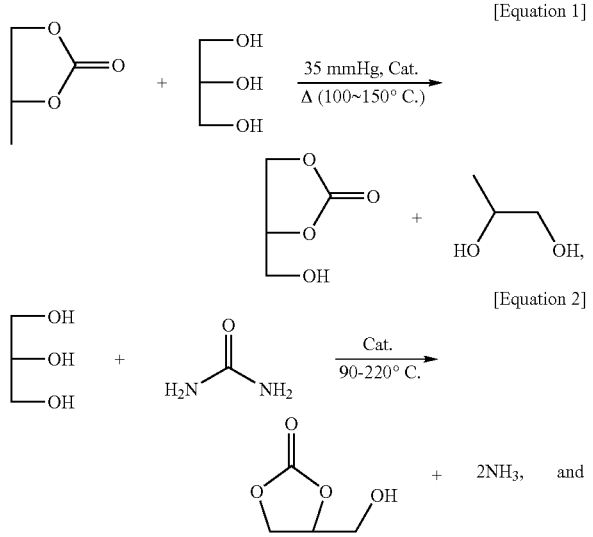

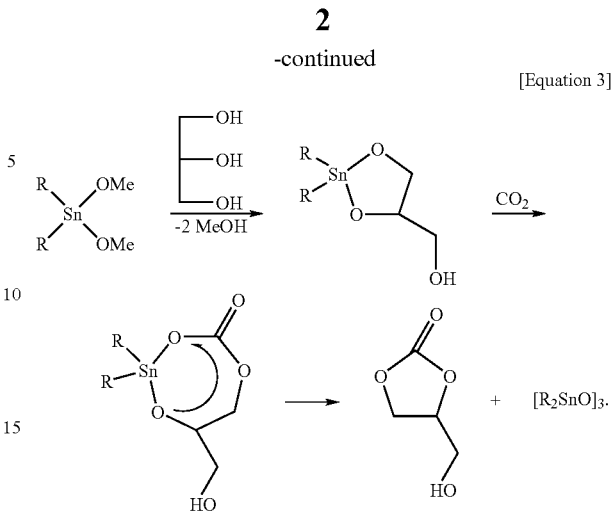

Here, Equation 1 is a reaction method (Huntsman synthesis method) in which ethylene carbonate (EC) or propylene carbonate (PC) is used as a reactant material, Equation 2 is a reaction in which urea is used as a reactant material, and Equation 3 is a two-stage reaction using carbon dioxide.

As described above, active utilizations of the byproducts of bio-diesel are highly required along with the expansion of the bio-diesel business. In particular, there is an urgent need for developing various derivative synthesis methods in which glycerol, having an advantage of being changeable into useful derivatives, is used as a reactant material. In particular, there is an urgent need for developing a more effective and stable synthesis method for synthesis of glycerol carbonate being excellent in its utilization.

DISCLOSURE OF INVENTION

Technical Goals

An aspect of the present invention provides a method of manufacturing more stable and higher-efficient glycerol carbonate (GC) for synthesizing glycerol carbonate using glycerol as a starting material.

Technical Solutions

According to an aspect of the present invention, there is provided a method of manufacturing glycerol carbonate (GC), including: a bio-catalyst reaction for generating the GC and byproducts generated by reacting a reactant solution using a lipase of a bio-catalyst, the reactant solution being prepared by adding glycerol, a glycerol-containing composition, or a dimethyl carbonate (DMC) in a reaction solvent.

In this instance, as the reaction solvent, tetrahydrofuran (THF), acetonitrile (AcCN), and tert-butanol (t-BuOH) may be used. Here, these reaction solvents may be used alone or any combination thereof.

Also, as the lipase, a candida antarctica lipase B (CalB) may be used.

Also, the bio-catalyst reaction may be preformed under an atmospheric pressure and at a temperature of about 40° C. to 70° C.

Also, a concentration of the lipase within the reactant solution before the bio-catalyst reaction may be preferably maintained with about 0.5 wt. % to 5.0 wt. %. In particular, to be maintained with about 0.5 wt. % to 1.5 wt. % may be advantageous in view of the processing efficiency.

Also, the bio-catalyst reaction may be additionally performed in the presence of a molecular sieve. In this instance, about 250 to 1000 parts by weight of the molecular sieve is contained within the reactant solution, relative to about 100 parts by weight of the GC or glycerol-containing composition.

Also, as the glycerol-containing composition, non-refined glycerol, that is, a crude glycerol may be used. In this instance, the crude glycerol may be preferably used in view of a yield of catalysis. Also, as the glycerol, glycerol of a byproduct generated upon synthesis of bio-diesel may be used.

Also, according to an aspect of the present invention, there is provided a method of manufacturing the GC, the method including: preparing a reactant solution by adding the GC, a glycerol-containing composition, or a dimethyl carbonate (DMC) in a reaction solvent of a tert-butanol (t-BuOH), also adding about 450 to 550 parts by weight of a molecular sieve in the t-BuOH, relative to about 100 parts by weight of the GC or glycerol-containing composition; and reacting the reactant solution at a temperature of about 40° C. to 70° C., under an atmospheric pressure, and under a concentration of about 0.8% to 1.2% of a lipase of a bio-catalyst for about 5 hours to 24 hours.

Advantageous Effects

There is provided a method of manufacturing glycerol carbonate (GC) according to exemplary embodiments which may exhibit an excellent stability of the reaction and significantly high processing efficiency. Also, the method of manufacturing GC according to exemplary embodiments may provide a more environmental-friendly processing atmosphere by using a lipase of a bio-catalyst.

BEST MODE FOR CARRYING OUT THE INVENTION

Figure 1:
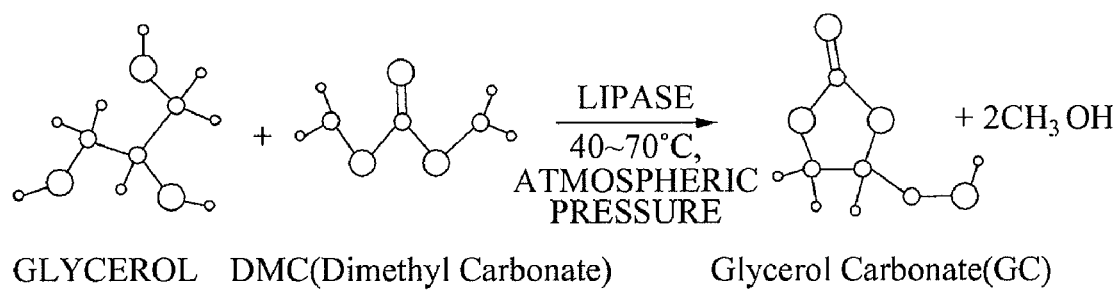
FIG. 1 is an equation schematically showing a synthesis method of glycerol carbonate (GC) according to an exemplary embodiment of the invention.

Reference will now be made in detail to embodiments of the present invention, examples of which are illustrated in the accompanying drawings, wherein like reference numerals refer to the like elements throughout. The embodiments are described below in order to explain the present invention by referring to the figures.

A method of manufacturing glycerol carbonate (GC) according to an exemplary embodiment of the invention includes a bio-catalyst reaction for generating the GC and byproducts generated by reacting a reactant solution using a lipase of a bio-catalyst. In this instance, the reactant solution is prepared by adding glycerol, a glycerol-containing composition, or a dimethyl carbonate (DMC) in a reaction solvent.

The glycerol designates refined glycerol, and the glycerol-containing composition designates non-refined glycerol including ingredients other than glycerol, such as a crude glycerol, and the like. Also, the glycerol is an expansive concept including a glycerol precursor in which glycerol may be generated in the reaction process.

FIG. 1 is an equation schematically showing a synthesis method of GC according to an exemplary embodiment of the invention.

Referring to FIG. 1, glycerol acting as a reactant material is reacted with DMC at about 40° C. to 70° C. and under an atmospheric pressure to thereby generate GC. This reaction is performed using a lipase acting as a bio-catalyst.

When the reaction temperature is about 40° C. or less, the reaction may be not performed, and when the reaction temperature is about 70° C. or more, the processing efficiency is dramatically reduced.

As shown in FIG. 1, the refined glycerol itself may be used, and a composition type-precursor mixture consisting of a plurality of ingredients, such as the crude glycerol, may be also used. In particular, in a case of using the crude glycerol, various byproducts are reacted under the lipase acting as a bio-catalyst, thereby showing an increase in a reaction yield.

Also, as the glycerol, glycerol of a byproduct generated in a bio-diesel synthesis process may be used, thereby effectively coping with the over supply of the glycerol in accordance with the expansion in the bio-diesel business.

As the reaction solvent, tetrahydrofuran (THF), acetonitrile (AcCN), and tert-butanol (t-BuOH) may be used. In this instance, these reaction solvents may be used alone or any combination thereof. In particular, t-BuOH may be preferably used in view of a yield and processing efficiency of the glycerol carbonate.

A concentration of the bio-catalyst is preferably about 0.5 wt. % to 5 wt. %, and more preferably about 0.5 wt. % to 1.5 wt. % in view of the processing efficiency.

A conversion ratio in which glycerol is converted into the glycerol carbonate becomes nearly saturated when a concentration of the lipase is about 0.5 wt. %, and a yield continuously increases to about 1.5 wt. % of the concentration of lipase. However, preferably, the concentration of lipase may be maintained to be about 1.5 wt. % or less in terms of the processing efficiency.

Preferably, the bio-catalyst reaction is performed in the presence of a molecular sieve in terms of the yield. The molecular sieve is preferably contained in a reactant solution in the amount of about 250 to 1,000 parts by weight based on about 100 parts by weight of the glycerol or glycerol-containing composition.

The molecular sieve may function to effectively remove methanol of a byproduct, thereby realizing a forward reaction in terms of the chemical equilibrium.

In accordance with researches of the present applicant, when the concentration of the lipase in the reactant solution is about 0.8% to 1.2%, and the concentration of the molecular sieve is about 450% to 550% relative to the concentration of the glycerol, the yield is maximized.

Also, advantageously, the glycerol may be generated as a byproduct when the crude glycerol is used as the glycerol-containing composition, so that a conversion ratio and yield of the glycerol carbonate may be dramatically increased. As described above, the crude glycerol is a non-refined glycerol, and includes other ingredients other than the glycerol.

Hereinafter, the present invention will be described in detail by examples. It is to be understood, however, that these examples are for illustrative purpose only, and are not construed to limit the scope of the present invention.

EXAMPLE

In estimations below, Candida Antarctica Lipase B (CalB) was used as the lipase, and 3A (TYPE 3A) manufactured by SAMCHUN chemical was used as the molecular sieve.
First Estimation of Conversion Ratio and Yield of Glycerol Mean values of a conversion ratio and yield varying based on a combination of all factors with respect to levels 1 to 3 as shown in Table 1 below, that is, based on the number of cases of 81 (3×3×3×3=81) were respectively produced, and mean values for each level were calculated.

TABLE 1

| Factors | Level | | |
|---|---|---|---|
| | 1 | 2 | 3 |
| Reaction temperature (° C.) | 60 | 70 | 80 |
| Bio-catalyst (wt. %) | 0.1 | 0.5 | 1.0 |
| Type of solvent | THF | AcCN | t-BuOH |
| Reaction time (hrs) | 5 | 10 | 24 |

Figure 2:
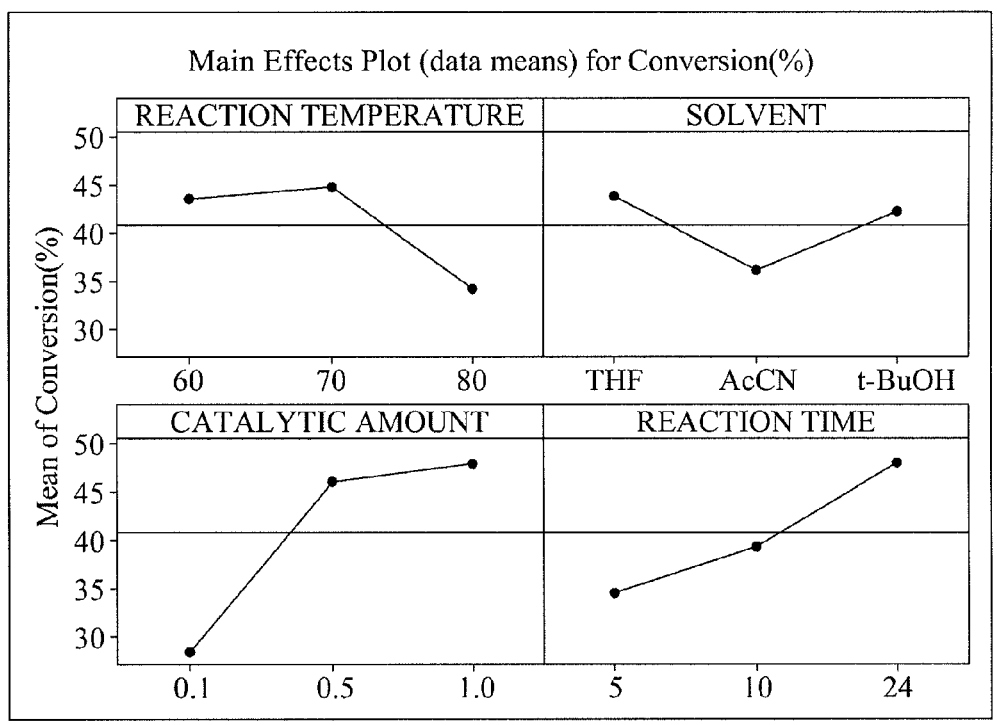
FIG. 2 is a graph showing a mean value of a conversion ratio (%) with respect to changes in a reaction temperature, a catalyst concentration, a type of solvent, and a reaction time according to an exemplary embodiment of the invention.
Figure 3:
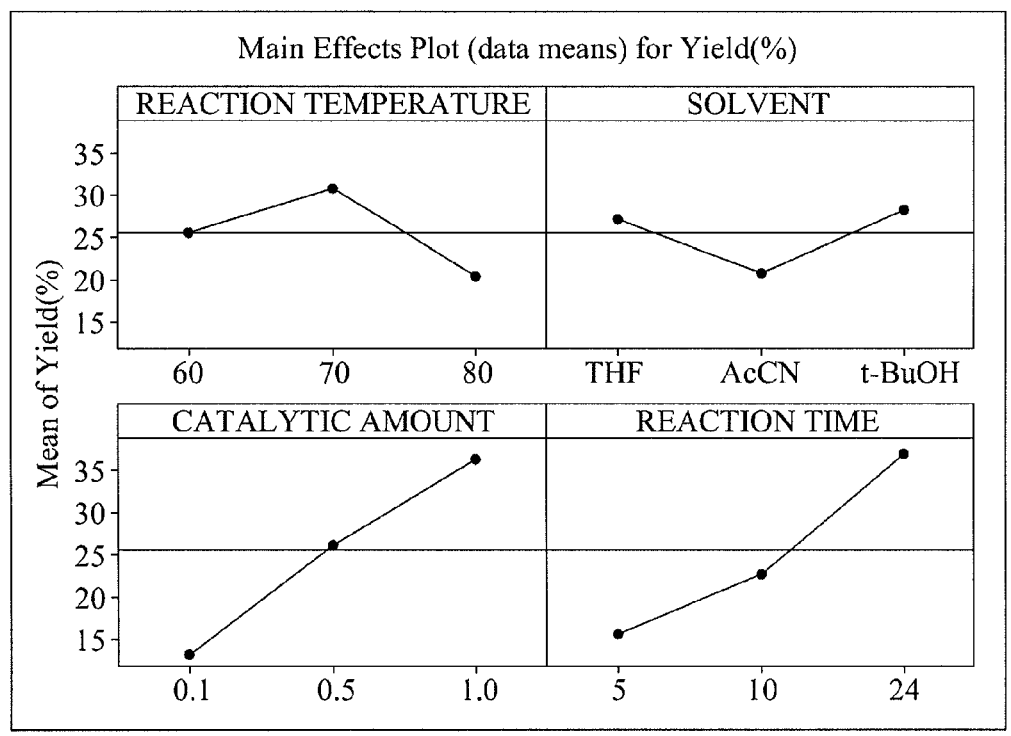
FIG. 3 is a graph showing a mean value of a yield (%) with respect to changes in a reaction temperature, a catalyst concentration, a type of solvent, and a reaction time according to an exemplary embodiment of the invention.

FIG. 2 is a graph showing a mean value of conversion ratio (%) with respect to changes in a reaction temperature, a catalyst concentration, a type of solvent, and a reaction time according to an exemplary embodiment of the invention, and FIG. 3 is a graph showing a mean value of a yield (%) with respect to changes in a reaction temperature, a catalyst concentration, a type of solvent, and a reaction time according to an exemplary embodiment of the invention.

Referring to FIGS. 2 and 3, the conversion ratio and yield are reduced when the reaction temperature exceeds about 70° C.

Also, an increase in the conversion ratio is slowed while an amount of the catalyst exceeds about 0.5 wt. %, however, an increase in the yield is continuously shown.

As for the reaction solvent, THF and t-BuOH have a relatively higher conversion ratio and yield in comparison with AcCN, however, there is no dominance between THF and t-BuOH. Accordingly, t-BuOH may be a more suitable solvent in synthesis of GC according to the present invention in view of costs of the reaction solvents.

Meanwhile, the conversion ratio and yield increases along with an increase in the reaction time. However, the reaction time may be preferably 24 hours or less in terms of the processing efficiency.
Second Estimation of Conversion Ratio and Yield of Glycerol Based on the first estimation, mean values and a conversion ratio and yield with respect to each factor as shown in Table 2 below were measured in a case where the reaction temperature was about 70° C., t-BuOH was used as the reaction solvent, and a molecular sieve (M. Sieve) was additionally contained in the reaction solvent. Similar to the first estimation, in order to produce a mean value of the combination of all factors for each level, a total of 27 data was produced. Meanwhile, an amount of the catalyst was determined to have a concentration of about 0.5% or more based on the first estimation results.

TABLE 2

| Factors | Level | | |
|---|---|---|---|
| | 1 | 2 | 3 |
| Bio-catalyst (wt. %) | 0.5 | 1.0 | 2.0 |
| Molecular sieve (wt. %) | 0 | 250 | 500 |
| Reaction time (hrs) | 5 | 10 | 24 |

Figure 4:
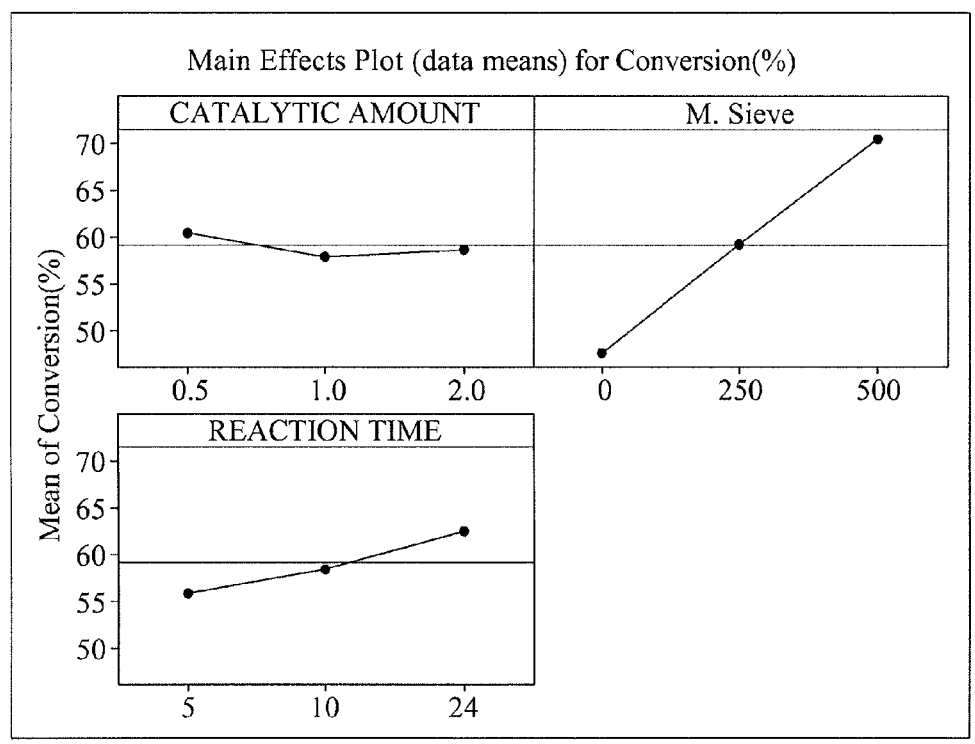
FIG. 4 is a graph showing a mean value of a conversion ratio (%) with respect to changes in a catalyst concentration, a molecular sieve concentration, and a reaction time according to an exemplary embodiment of the invention.
Figure 5:
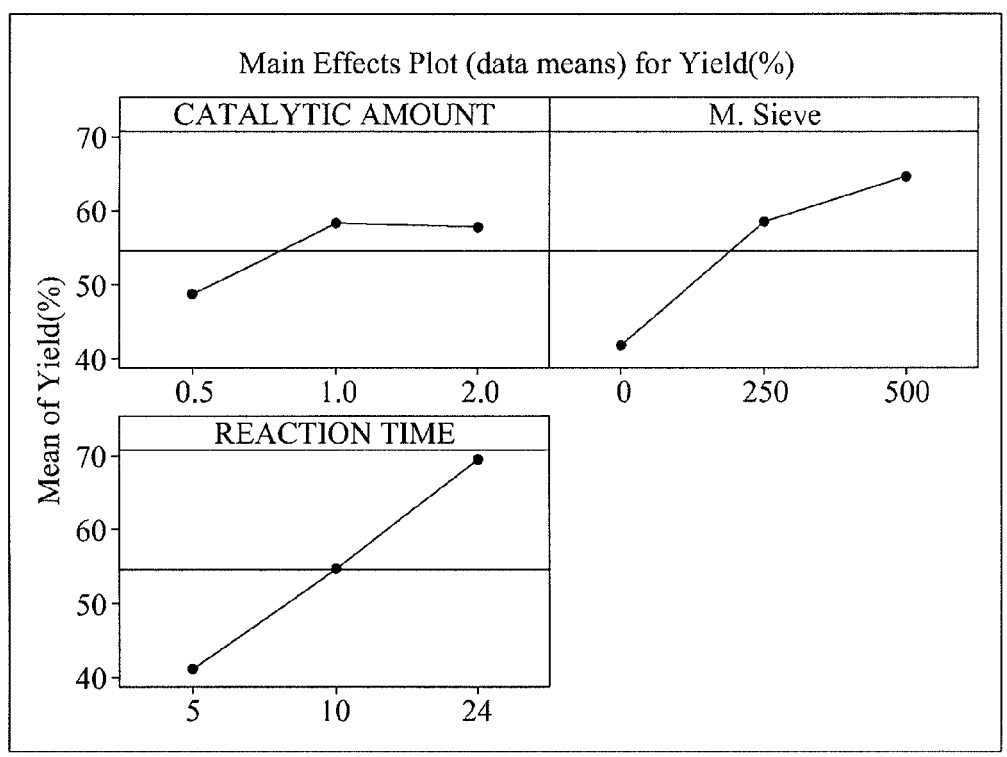
FIG. 5 is a graph showing a mean value of a yield (%) with respect to changes in a catalyst concentration, a molecular sieve concentration, and a reaction time according to an exemplary embodiment of the invention.

FIG. 4 is a graph showing a mean value of a conversion ratio with respect to changes in a catalyst concentration, a molecular sieve concentration, and a reaction time according to an exemplary embodiment of the invention, and FIG. 5 is a graph showing a mean value of a yield (%) with respect to changes in a catalyst concentration, a molecular sieve concentration, and a reaction time according to an exemplary embodiment of the invention.

Referring to FIGS. 4 and 5, when the molecular sieve is used, both of the conversion ratio and yield increase. Also, the conversion ratio becomes nearly saturated for about 5 hours, however the yield continuously increases over time. Also, the conversion ratio and yield increase along with an increase in the concentration of the molecular sieve.

Figure 6:
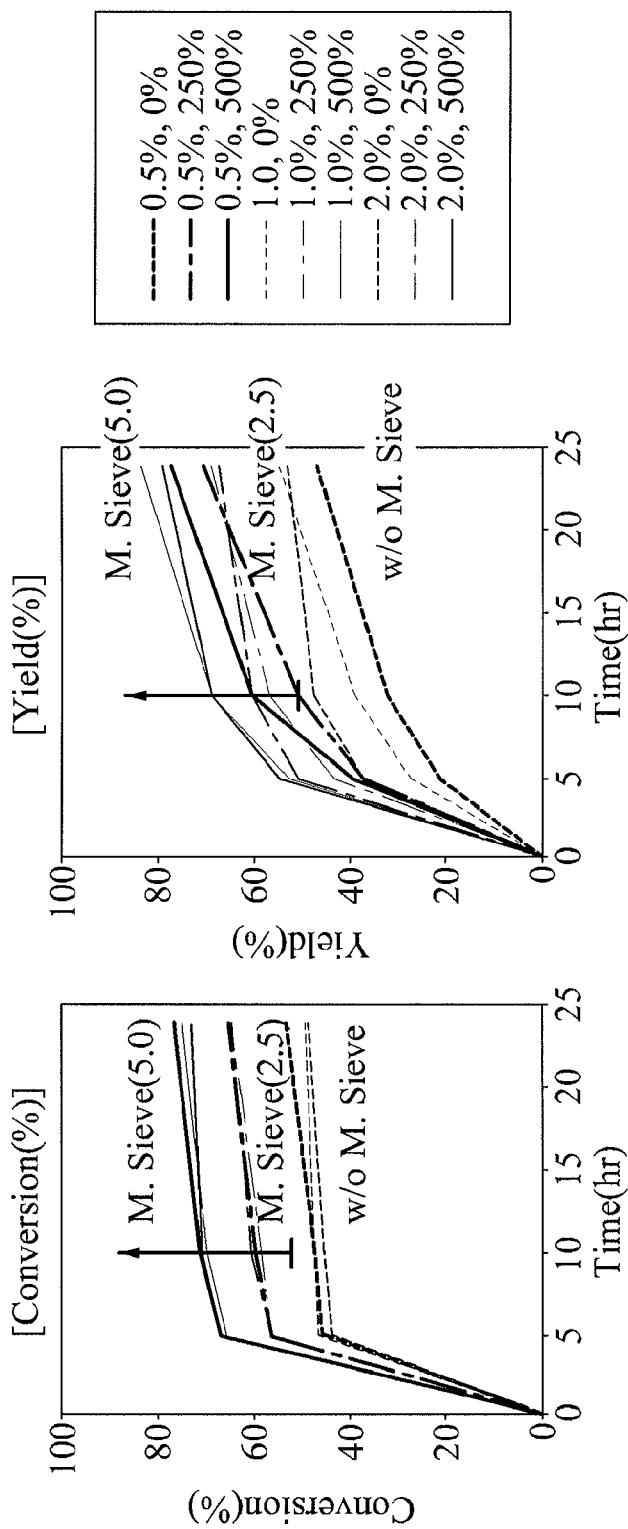
FIG. 6 is a graph showing changes in a conversion ratio and yield over time with respect to all combinations of a catalyst concentration and molecular sieve concentration according to an exemplary embodiment of the invention.

FIG. 6 is a graph showing changes in a conversion ratio and yield over time with respect to all combinations of a catalyst concentration and molecular sieve concentration according to an exemplary embodiment of the invention.

Referring to FIG. 6, the conversion ratio becomes nearly saturated when exceeding about 5 hours, however the yield continuously increases. Also, the increase in the yield is also dramatically slowed after about 10 hours.

Accordingly, maintaining the reaction time for about 10 hours may be effective in view of the processing efficiency.

Also, in the second estimation, the conversion ratio and yield are maximized when the reaction is performed under the concentration of catalyst of about 1.0% and the concentration of molecular sieve of about 500 wt. % relative to a weight of glycerol.

Accordingly, in view of experimental errors, the yield may be maximized when the concentration of catalyst is about 0.8% to 1.2% and an amount of molecular sieve is about 450 to 550 parts by weight relative to about 100 parts by weight of the glycerol. As described above, in view of the processing efficiency, the reaction time may be preferably within about 24 hours, and more preferably about 10 hours.
GC Synthesis Using Crude Glycerol A crude glycerol of two companies having a composition shown in Table 3 below was used as a starting material. GC was synthesized according to experimental conditions shown in Table 4 below and a conversion ratio and yield was estimated.

TABLE 3

| CAS Number | Components | A company | B company |
|---|---|---|---|
| 67-56-1 | methanol | 1.7% | 10 to 15% |
| 1310-73-2 | NaOH | 2.1% | — |
| 100299-02-3 | Bio-diesel | 1.8% | <15% |
| 7732-18-5 | Water | 4.3% | 1 to 5% |
| — | Soap | 15.7% | 10% |

TABLE 3-continued

| CAS Number | Components | A company | B company |
| --- | --- | --- | --- |
| 61788-66-7 | Vegetable oil | 0.43% | |
| 56-81-5 | Glycerin | 72.5% | 75 to 85% |

TABLE 4

| Reaction temperature (° C.) | Time (hrs) | Solvent | Molecular sieve (wt. %) | Bio-catalyst (wt. %) |
| --- | --- | --- | --- | --- |
| 70 | 10 | t-BuOH | 500 | 1.0 |

Figure 7:
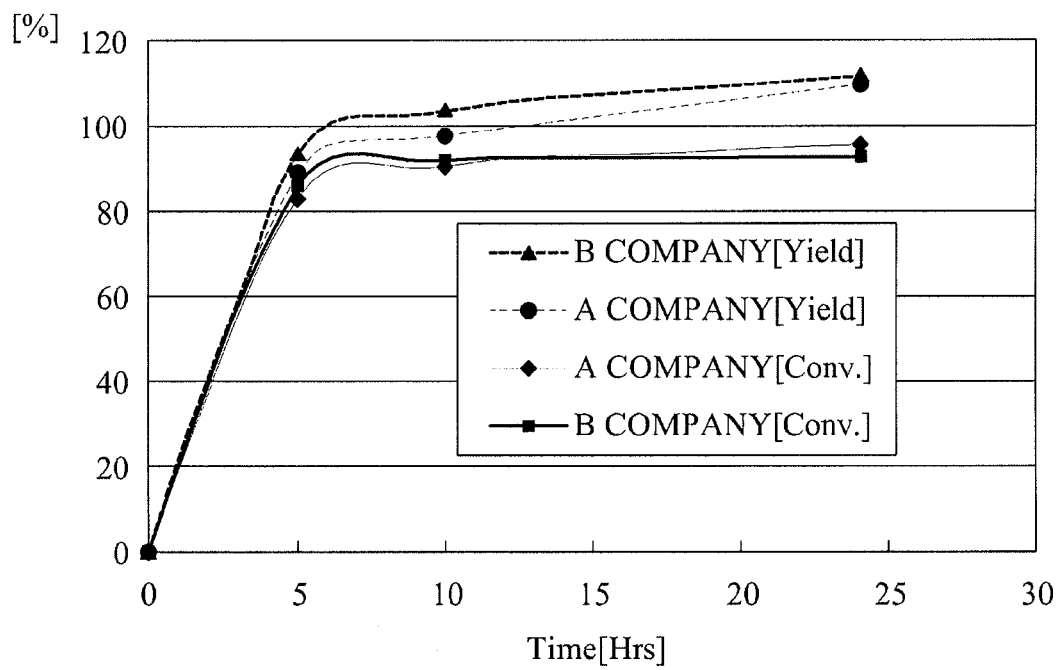
FIG. 7 is a graph showing changes in a conversion ratio and yield over time as results of GC synthesis of two companies having a composition of Table 3 using a crude glycerol according to an exemplary embodiment of the invention.

FIG. 7 is a graph showing changes in a conversion ratio and yield over time as results of GC synthesis of two companies having a composition of Table 3 using a crude glycerol according to an exemplary embodiment of the invention.

Referring to FIG. 7, the conversion ratio and yield are higher in a case of using the crude glycerol than those in a case of using the refined glycerol. This is because the glycerol may be generated as a byproduct according to the reaction of the crude glycerol.

Also, the conversion ratio and yield becomes semi-saturated when exceeding about 5 hours, and then a gentle increase in the conversion ratio and yield is shown.

On a basis of about 10 hours, the conversion ratio and yield are respectively about 91.0% and 97.5% when using the crude glycerol of the company A. Also, the conversion ratio and yield are respectively about 86.0% and 103.6% when using the crude glycerol of the company B.

Accordingly, the conversion ratio and yield when using the crude glycerol are relatively higher in comparison with when using the refined glycerol.

Industrial Applicability

As described above, according to the present invention, the method of manufacturing the glycerol derivative and the revitalization of the bio-diesel are very useful in the industries, which may be expected to be specifically achieved in the corresponding fields.

In particular, the present invention may be very much in line with current environmental-friendly trend as well as recycle of resources.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

The invention claimed is:

1. A method of manufacturing a glycerol carbonate (GC), the method comprising:
    adding crude glycerol and dimethyl carbonate (DMC) to a reaction solvent to form a reaction solution; and
    reacting the reactant solution with a lipase bio-catalyst to form the glycerol carbonate.

2. The method of claim 1, wherein the reaction solvent contains at least one compound selected from a group consisting of tetrahydrofuran (THF), acetonitrile (AcCN), and tent-butanol (t-BuOH).

3. The method of claim 1, wherein the lipase is a candida antarctica lipase B (Ca1B).

4. The method of claim 1, wherein the reaction is performed under an atmospheric pressure and at a temperature of about 40° C. to 70° C.

5. The method of claim 1, wherein a concentration of the lipase within the reactant solution before the reaction is about 0.5% to 1.5%.

6. The method of claim 1, wherein the reaction is additionally performed in the presence of molecular sieves.

7. The method of claim 6, wherein about 250 to 1,000 parts by weight of the molecular sieves is present within the reactant solution, relative to about 100 parts by weight of crude glycerol.

8. The method of claim 1, wherein
    the reaction solvent is tert-butanol (t-BuOH), and about 450 to 550 parts by weight of molecular sieves is added to the reaction solution relative to about 100 parts by weight of crude glycerol; and
    the reaction is performed at a temperature of about 40° C. to 70° C under an atmospheric pressure, and with a concentration of about 0.8% to 1.2% of lipase bio-catalyst for about 5 hours to 24 hours.

* * * * *